United States Patent [19]

Roberts

[11] 4,056,967

[45] Nov. 8, 1977

[54] PNEUMATIC SYSTEM FOR A GAS SENSOR

[75] Inventor: John A. Roberts, Lynnfield, Mass.

[73] Assignee: General Electric Company, Schenectady, N.Y.

[21] Appl. No.: 705,988

[22] Filed: July 16, 1976

[51] Int. Cl.$^2$ ............................................. G01N 31/00
[52] U.S. Cl. ...................................................... 73/1 G
[58] Field of Search ...................... 73/1 G, 23, 61.1 R, 73/421.5 R

[56] References Cited

U.S. PATENT DOCUMENTS

| 3,188,854 | 6/1965 | Hersch | 73/23 |
| 3,975,947 | 8/1976 | Kruishoop | 73/61.1 |

Primary Examiner—S. Clement Swisher
Attorney, Agent, or Firm—Vale P. Myles

[57] ABSTRACT

A pneumatic system for controlling admission of gas samples to a toxic gas monitoring sensor, characterized by including an internally isolated, series pneumatic circuit for continuously circulating purging gas through the sensor, in combination with a gas sampling circuit for introducing gas samples from one or more sources into the relatively isolated series circuit. The gas sampling circuit is further characterized by including a calibration loop having a standard gas leak that is periodically energized to assure the accuracy of readings indicated by the gas sensor in the internal isolated series loop. Also, the gas sampling circuit includes a zero gas source that is selectively operable to feed purifying gas into the gas sampling circuit and thence to the series circuit including the sensor in order to enable flow meters in the system to be calibrated periodically.

18 Claims, 1 Drawing Figure

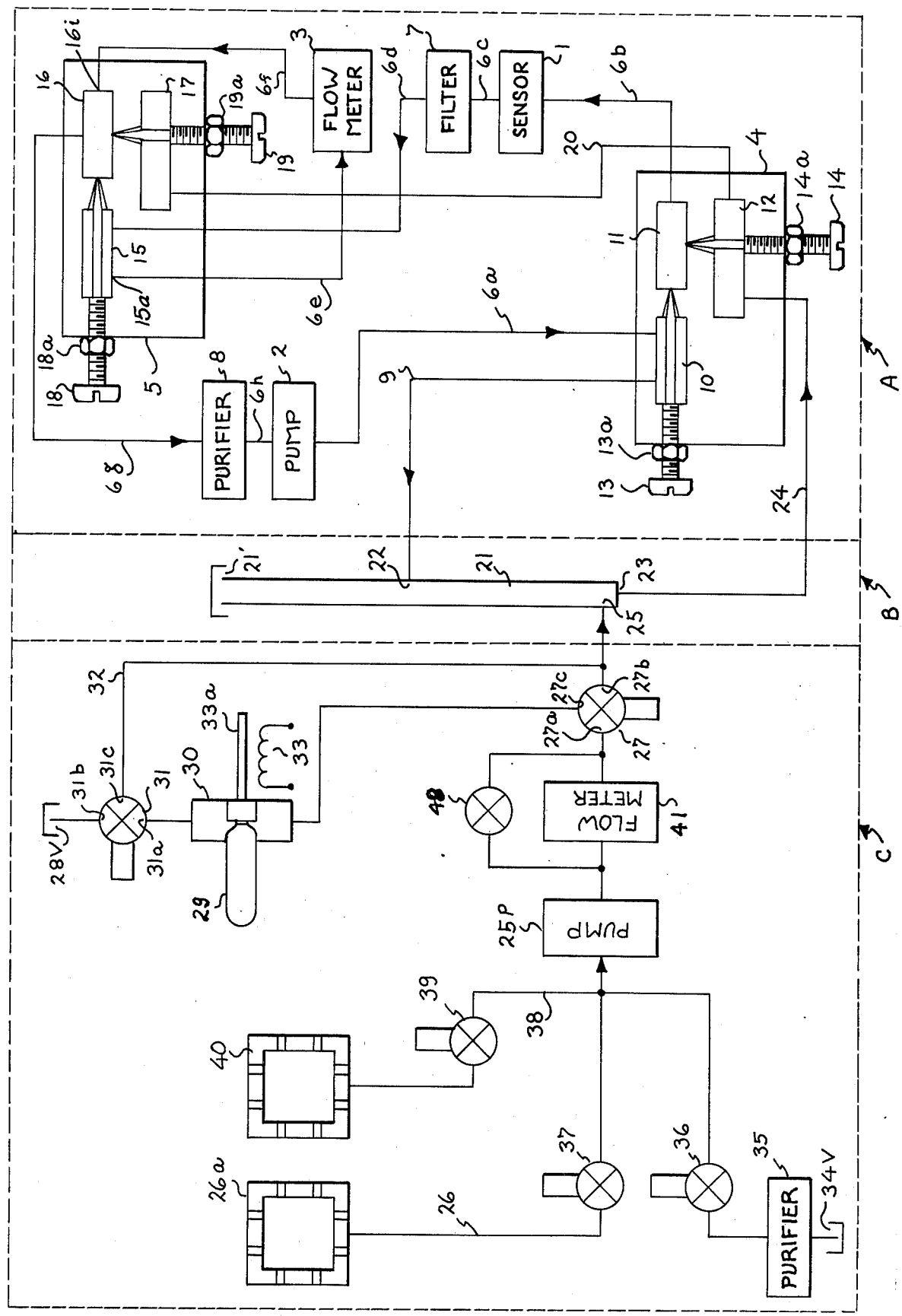

PNEUMATIC SYSTEM FOR A GAS SENSOR

BACKGROUND OF THE INVENTION

The invention relates to toxic gas monitors of a type that are useful in continuously monitoring threshold limit values of toxic gases that may be found in certain occupational and industrial environments. More particularly, the invention relates to a pneumatic system for controlling the admission of atmospheric gas samples to a monitoring sensor at levels that are compatible with the linear range of the sensor indicating means. The pneumatic system also includes means for quickly and easily calibrating the sensor and zeroing the indicating meters on a periodically repeatable basis, and further includes convenient means for monitoring a plurality of sampled input areas sequentially and continuously with a single sensor element in the system.

A variety of different types of gas sensors are commercially available for detecting and recording the presence of very low concentrations, i.e., in the range of one-tenth part to two or three parts per million, of toxic gas present in an atmospheric sample. The use of such sensors in underground mines where poisonous gas concentrations are often encountered suddenly due to the release of trapped gas from underground pockets is one example of a common early application for such sensors. In the last few years, the use of such toxic gas monitors has increased sharply due to a growing awareness of long-term health hazards that may be caused by extended exposure to heretofore acceptably low concentrations of certain toxic gases. In fact, various laws have been passed which now specify a range of threshold limit values, commonly referred to as TLV's, that cannot be exceeded for extended time periods in given occupational and industrial environments without subjecting those in control of the area to legal penalties. Examples of such specifications are those promulgated by the National Institute of Safety and Health (NIOSH) under the provisions of the Occupational Safety & Health Act of 1970 that is currently in effect in the United States. The nature of such laws and their associated TLV specifications frequently requires that many working and occupational environments be continuously monitored by very sensitive toxic gas sensors to assure that a suitable warning and/or record of the presence of toxic gases in excess of the TLV's does not occur for undesirably long periods in such monitored environments.

Responsive to this growing need for continuously operable, highly reliable and relatively sensitive gas monitoring apparatus, a number of different types of toxic gas monitoring systems have been developed. While such prior art systems have been found generally suitable for their intended application, they have several disadvantages or drawbacks in common. One of the most common problems encountered with such sensitive gas monitoring sensors is their susceptibility to having associated indicating instruments driven off scale due to unusually heavy concentrations of toxic gases occurring periodically in a sampled atmosphere. In addition to causing loss of accurate qualitative analysis of the samples taken during such intervals when the scale is overdriven, the monitoring sensor may be partially saturated and thus, at least temporarily, rendered inaccurate by the overdose of monitored toxic gas so that it might fail to detect successive samples. A second disadvantage of known prior art sensor systems is that they are normally limited to use in a single sampling location, rather than being readily adaptable to continuously and rapidly monitor a plurality of different environments in sequence.

It has also been found that in order to assure continuous reading precision of the degree often desired on toxic gas monitors that are to be placed in constant industrial environment sampling use, it is desirable to both periodically calibrate the sensor elements of the monitors against a standard gas leak, and periodically zero the sensor instruments by introducing a purified or "zero" gas into the monitoring system. A difficulty frequently encountered when attempting to implement such calibrating procedures on known prior art gas sensors is that considerable time and effort is needed to sufficiently purge the sensor systems of remnants of toxic gases sampled earlier, in order to enable accurate calibration and zero meter setting of the sensors. This same problem of lingering gases in the sensor systems, due to inadequate purging means for quickly and continuously cleansing the systems after each sample is monitored, prevents many prior art sensors from being readily adaptable to rapidly and sequentially monitor a plurality of different atmospheric environments.

OBJECTS OF THE INVENTION

Accordingly, it is a primary object of the present invention to provide a toxic gas sensor having a pneumatic system that overcomes the above-noted disadvantages of known prior art toxic gas monitoring arrangements.

Another object of the invention is to provide a pneumatic system for controlling the admission of gas samples to a gas sensor so that a plurality of different ambient environments may be sampled rapidly and reliably in sequence using a single sensor element, the indicating readings of which are maintained within the linear scale range of the indicating instruments in the system.

A further object of the invention is to provide a gas sensor having a gas sampling circuit including a zero gas input and a standard gas leak calibration means.

A major object of the invention is to provide a gas monitoring sensor having a gas sampling circuit that is periodically isolated from a continuously operated internal series circuit that flushes purging gas through a sensor element of the monitoring system.

Still another object of the invention is to provide a gas monitoring system that is relatively economical to manufacture, efficient to operate, and highly reliable for accurately sensing and recording a few parts per million of given toxic gases in one or more of a plurality of separate sources of monitored sample gases.

Additional objects and advantages of the invention will become apparent to those skilled in the art from the description of it that follows taken in connection with the accompanying drawing.

SUMMARY OF THE INVENTION

In one preferred embodiment of the invention a toxic gas monitor is provided having a pneumatic system for controlling admission of sample gases to a gas sensor in the monitor. The pneumatic control system of this embodiment of the invention includes a series loop circuit that is operable to continuously pump a fixed displacement flow of purging gas through a sensor and a flow meter, as well as thrugh the chambers of two manifold controlling valves thereby to maintain the sensitivity of the sensor circuit. In combination with this relatively isolated internal series loop circuit, the monitor includes a gas sampling circuit having an input pump and a control valve arrangement that operates in conjunction with a standard gas leak source and valve regulated zero gas source to afford means for quickly and repetitively calibrating the gas sensor of the monitor and for periodically zeroing the indicating instrument of the system.

BRIEF DESCRIPTION OF THE DRAWING

The sole FIGURE of the drawing is a schematic diagram of a toxic gas monitor including a pneumatic system for controlling admission of gas samples to a sensor element, in combination with a gas sampling input circuit having means for introducing a zero gas to the monitor for periodically setting or "zeroing" the indicating instruments of the monitor system, as well as a standard gas leak for repetitively calibrating the sensor of the monitor.

DESCRIPTION OF THE PREFERRED EMBODIMENT

Referring now to the sole FIGURE of the drawing, it will be seen that there is shown a schematic circuit diagram of a gas monitor system including components and connections arranged in accordance with the teaching of the present invention. To facilitate the description of this preferred embodiment of the invention, three basic characteristic sub-assemblies of the gas monitor are designated by three dashed box outlines lettered respectively A, B and C at the lower portion of the drawing. The portion of the gas monitor within the box A comprises a series loop circuit that is operable to continuously purge a gas sensor element in a manner that will be more fully described below. The portion of the monitor shown within the Box B comprises a gas sample input chamber that is connected pursuant to the invention to receive gas from both the isolated series loop circuit within the box A and from one or more sampled environments through a gas sampling circuit arrangement and calibrating means contained with the box C.

Rather than initiating the description of the component parts of the preferred embodiment of the invention with a discussion of the gas sampling circuit C as might seem logical due to its function of providing input samples that are to be monitored by the sensor of the monitoring system, a description of the isolated internal series loop circuit A of the monitor will first be presented in order to illustrate its characteristic advantages and particular functions so the reader may better appreciate the objectives and operations of the remaining sub-assemblies of the system. Thus, referring particularly to the components of the gas monitor illustrated within the box A in the drawing, it will be seen that the series loop circuit includes a gas sensor 1, a first pump 2, a flow meter 3, a first manifold valve 4, and a second manifold valve 5, all of which are connected in a pneumatic series circuit loop by a plurality of suitable tubular conduits designated, respectively, by the alpha-numerics 6a, 6b, 6c, 6d, 6e, 6f, 6g and 6h. In addition to these basic component parts of the pneumatic system for controlling admission of gas samples to the sensor 1, pursuant to the invention, the preferred embodiment of the invention herein described includes a filter 7 connected in series between the sensor 1 and the second manifold valve 5, and a purifier 8 connected in series between the conduit 6g and 6h, before the pump 2.

As the description of this embodiment of the invention proceeds, those skilled in the art will recognize that various reltively standard component parts may be used to provide the functions of the respective components in the series loop circuit discussed thus far; however, by way of example, it should be noted that in the presently preferred embodiment of the invention the sensor 1 is a commercially available halogen gas sensor sold by the Instrument Products Operation of General Electric Company located in Lynn, Massachusetts. Such halogen sensors are offered for sale under Catalogue No. 6614K11001. Of course, if other types of gases such as methane or acetone are to be monitored in given applications of the invention, suitable different gas sensors would be substituted in the described system for the illustrated sensor 1.

A constant displacement pump, of the type shown here as pump 2, is also available from the same source under Catalogue No. 5932K10001. It is important to understand that in order for the isolated series loop circuit to perform properly while continuously monitoring a plurality of sources of sampled gas in the manner that will be described hereafter, the pump 2 is synchronously driven by a conventional synchronous motor so that a stable flow of gas is maintained in the conduits 6a–6h. More specifically, in one preferred form of the invention the pump 2 is operated at a synchronous rate such that a flow of about 4 cubic centimeters per second of gas is maintained in the conduit 6b of the series loop circuit A, just upstream from the sensor 1. At the same time, the needle valve (14) in the first manifold valve 4 is preferably adjusted so that about one-half cubic of gas per second of gas is allowed to flow out of the series loop circuit through a conduit 9 for a purpose that will be described more fully later. The flow meter 3 used in the preferred embodiment of the invention is also available from the same commercial source under the Catalogue No. 5224K90001. Any suitable commercially available felt-type dust filter may be used for the filter 7 in order to protect the second manifold valve 5 and the flow meter 3 from blockage and contamination by particulate matter that might be brought into the series circuit A with a monitored gas sample introduced into it. Finally, the air purifier 8 used in this form of the invention is a commercially available purifier marketed under the name "Koby" by Koby Inc., of Marlboro, Massachusetts.

As can be seen from the drawing, the first and second manifold valves 4 and 5, respectively, contain closely similar component parts and thus may be machined from standard steel stock and provided with relatively conventional needle valves to afford the desired functions of the invention that will be described in greater detail after the characteristic features of these valves are discussed. Considering first the first manifold valve 4, it will be seen that it contains a first chamber 10, a second chamber 11, and a third chamber 12. A first adjustable needle valve 13 is disposed to control gas flow between the first chamber 10 and the second chamber 11. Likewise, a second adjustable needle valve 14 is disposed to control gas flow between the second chamber 11 and the third chamber 12. In the operation of the manifold valve 4, it is desirable to set these respective flow rates between the chambers of the valve at given levels, therefore, the needle valves 13 and 14 are provided with suitable locking means, such as the lock nuts 13a and 14a, to secure the needle valves in desired positions for a selected application of the system. As indicated above, a suitable relative flow rate between the first chamber 10 and the second chamber 11 of first manifold valve 4 will be about 3½ cubic centimeters per second, in order to maintain a flow rate of approximately four cubic centimeters per second through the conduit 6b to the sensor 1. Thus, the excess gas supplied to the manifold valve 4 by conduit 6a will go through the first chamber 10 of the manifold valve into a bypass conduit 9 at a rate of approximately ½ cubic centimeter per second, plus any flow admitted by valve 19. Obviously, other relative flow rates may be selected for different applications of the system.

The second manifold valve 5 is of somewhat similar construction, including a first chamber 15, a second chamber 16, and a third chamber 17; with a first adjustable needle valve 18 disposed to control gas flow between the first chamber 15 and the second chamber 16, and with a second adjustable needle valve 19 disposed to control gas flow between the third chamber 17 and the second chamber 16. Again, any suitable locking means (18a and 19a) may be used to secure needle valves 18 and 19 in fixed operating positions.

In order to prevent the pump 2 from being "starved" and to provide for continuously purging the sampled gas inlet chamber of the system, which is the third chamber 12 in the first manifold valve 4, a bleeder line conduit 20 is operably connected between the respective third chambers of the first manifold valve 4 and the second manifold valve 5 to bypass some gas around the sensor 1. The operation of the bypass-bleeder line 20 may be more readily appreciated if the description of the invention is now enlarged to include the gas sample input chamber shown in the dashed box B of the drawing.

As illustrated, a vented gas sample input chamber 21 having a loosely covered vent 21' to the ambient atmosphere is provided with an overflow gas input orifice 22 that is connected to receive gas flowing through the conduit 9 from a suitable point in the series loop circuit A between the pump 2 and the first flow restricting needle valve 13 in the first manifold valve 4. As indicated earlier, in this embodiment of the invention such a suitable point is an unregulated outlet orifice 10a in the first chamber 10 thereof. Input chamber 21 further includes an outlet orifice 23 connected to deliver gas through a conduit 24 to the third chamber 12 of the first manifold valve 4. Finally, the vented input chamber 21 includes a sample gas inlet orifice 25 that is disposed in the chamber between the overflow input orifice 22 and the outlet orifice 23 and is operable to deliver a gas sample to the input chamber 21 from the sampling circuit C that will be described more fully hereafter.

It will be seen that since the input chamber 21 is vented to atmospheric pressure, that pressure will be substantially maintained in the first chamber 10 and the third chamber 12 of the first manifold valve 4. Accordingly, when the pump 2 is synchronously operated, in the manner described above pursuant to the present invention, a pressure of about 1 pound per square inch below atmospheric pressure will normally be maintained in the second chamber 11 of the first manifold valve 4. Due to this reduced pressure in the chamber 11, overflow gas that enters the sample gas input chamber 21 from conduit 9 will be drawn through the outlet orifice 23 into conduit 24 and then be delivered into the third chamber 12 from which it flows through needle valve 14 into the second chamber 11 of the first manifold valve, and through valve 19 into chamber 16 of valve 5. Similarly, the operation of pump 2 causes the gas to flow continuously through the sensor 1 to purge it and maintain it in condition to immediately receive and accurately sense subsequent threshold limit values of toxic gases that may be introduced into the isolated series loop (A) of the system through the orifice 25 in the sample gas input chamber 21.

It will also be appreciated that the interconnection between the respective third chambers 12 and 17 in the first and second manifold valves, via the bleeder line 20, serves to raise the pressure in the third chamber 17 of the second manifold valve 5 to approximately atmospheric pressure. Accordingly, gas will be continuously circulated from the third chamber 17 into the second chamber 16 in valve 5 and thence through conduit 6g and 6h into the pump to prevent the pump from being starved in the absence of the introduction of sample gas, through the input gas chamber 21, from the sample gas inlet orifice 25.

In order to adjust and set a desirable flow rate through flow meter 3, it will be seen that the first chamber 15 of the second manifold valve 5 is similar to the first chamber 10 of the first manifold valve 4 in that both of these first chambers are provided with an inlet orifice and an outlet orifice in addition to the needle valve regulated orifices therein which communicate with the respective second valve chambers 16 and 11. As indicated above, both of these unregulated inlet and outlet orifices are connected, respectively, to bypass gas around the needle valve regulated orifices between the first and second respective chambers of the manifold valves. By adjusting the needle valve 18 in the second manifold valve 5 it is possible to determine the rate of flow of gas through flow meter 3 at any desired level, as will be readily recognized by those skilled in the art. Of course, this is possible because the flow meter 3 is operably connected in the series loop circuit A between the unregulated outlet orifice 15a in the first chamber 15 in second manifold valve 5 and an inlet orifice 16i in the second chamber 16 of the manifold valve 5. For the form of the invention being described, a flow rate of about 2 cubic centimeters per second is set through flow meter 3. Preferably, the gas purifier 8 is operably connected in the series loop circuit A between the pump 2 and the outlet port 16b of chamber 16 to receive gas from second manifold valve 5.

From the foregoing description of the generally isolated internal series loop circuit A of the sensor of the preferred embodiment of the invention, it will be understood that this circuit can be precisely adjusted by regulating the needle valves in the two manifold valves 4 and 5 to establish and maintain a substantially constant flow rate of gas through the sensor 1 and flow meter 3. Thus, even when a sudden high concentration of toxic gas is introduced as a sample into the input chamber 21 and thence through conduit 24 into the third chamber 12 of the first manifold valve 4, the degree of intermixing between the sample and the gas in circuit A, as well as the rate of flow of the intermixed sample and circulating gas in the isolated loop circuit A is controlled by the bleeder line 20 and the setting of the needle valve 14 that controls the flow of sampled gas from the third chamber 12 into the second chamber 11 of the first manifold valve 4. With this precision control arrangement, it is possible to provide for the admission of a plurality of different gas samples, i.e., from different sampling locations, in rapid sequence while assuring that the atmospheric samples will be compatible with the linear range of the sensor and its indicating or recording means.

Turning now to the gas sampling circuit C that is used in combination with the vented gas sample input chamber arrangement B and the isolated series loop circuit A in the preferred embodiment of the invention, it will be seen by referring to the drawing that the sampling circuit C comprises a second pump 25p that is connected in series between a suitable gas sample inlet conduit 26 and a first three-way valve 27. In this form of the invention the pump 25p need not be a uniform displacement pump, such as the pump 22 in circuit A; however, in order to standardize the construction of the system, the pump 25p and the pump 22 are both constant displacement pumps. The pump 25p has a substantially larger displacement than the pump 2; particularly, if a plurality of different ambient gas sources are to be monitored by the system in a manner that will be described hereafter. A gas integrator 26a, which may be of any conventional form well-known in the art, but preferably is simply a perforated tank that is suitable for performing the desired integration function on the sampled gas is connected to the other end of inlet conduit 26.

Similarly, the three-way valve 27 may be a manually actuated valve or, as in the case being described, a solenoid controlled valve but it should be designed to have a single inlet 27a and one outlet 27b that is a normally closed outlet connected in communication with the sample gas inlet orifice 25 in the vented gas sample inlet chamber 21. In addition, the valve 27 should be provided with another outlet 27c that is normally open and in communication with a vent 28v to the ambient atmosphere. Pursuant to the present invention, the gas sampling circuit C (as thus far described) is combined with a calibrating circuit comprising a selectively operable standard gas leak 29 that is mounted to discharge its gas into a mixing chamber 30 that is connected in series between said other outlet 27c of the first three-way valve 27 and a second three-way valve 31 that has an inlet orifice 31a connected as shown in the drawing to the standard gas leak chamber 30. One of the outlets 31b of the three-way valve 31, which is a normally open outlet, is connected as shown to the embient atmosphere vent 28v. The other outlet 31c of valve 31 is connected in communication with the gas sample inlet orifice 25 of the vented gas sample input chamber 21 by a suitable conduit 32. The other outlet orifice 31c is a normally closed orifice in the preferred configuration of the valve 31.

In this form of the invention, the discharge of gas from the selectively operable standard gas leak 29 is controlled by the plunger 33a of an electric solenoid 33 that may be of any suitable conventional structure. Similarly, the first and second three-way valves 27 and 31 may be either manually controlled or solenoid actuated in various applications of the invention.

In the operation of the standard gas leak 29 to calibrate the sensor 1, it will be understood that the first and second three-way valves 27 and 31 are operated to pass all of the outlet gas from the second pump 25p into mixing relationship in the chamber 30 with the gas from the standard gas leak 29, due to their simultaneous operation with the control solenoid 33 that introduces gas from the standard gas leak into chamber 30. From the chamber 30 the calibrating gas is then passed through the conduit 32 and orifice 25 into the sample gas input chamber 21 and thence through conduit 24 into the series loop circuit A where it is detected by sensor 1. During this operation of the calibration circuit, first three-way valve 27 is actuated to open its normally-open outlet 27c and to maintain its normally-closed outlet 27b closed. Also, the second three-way valve 31 is operated to open its normally-closed outlet 31c and to close the outlet 31b so that none of the gas from the standard leak 29 is vented to the atmosphere through vent 28v. Due to the solenoid control of the standard gas leak, it is possible with this embodiment of the invention to periodically and repetitively introduce a series of standard gas leaks into the sensor 1 to accurately maintain its calibration, as desired when the system is used to continuously monitor environments such as those often found in industrial or occupational applications of the invention.

In addition to the calibrating circuit just described, the gas sampling circuit C of the preferred embodiment of the invention includes the combination of a zero gas circuit that is used to accurately calibrate the indicating instruments of the sensor system in the absence of any toxic sample gases. The zero gas circuit in this embodiment of the invention includes an ambient air input vent 34v that is connected in series with an air purifier 35 and a first on-off valve 36, which is connected in turn to the upstream side of the second pump 25p as shown in the drawing. The air purifier 35 may be of any conventional design such as that of the crushed charcoal purifier 8 described more fully above. In this form of the invention the first on-off valve 36 is a solenoid actuated valve of conventional design, but a manually operated valve could be used in other applications of the invention.

To facilitate the operation of the zero gas circuit, the gas sampling circuit is provided with a second on-off, solenoid actuated valve 37 that is connected in series between the second pump 35p and the gas sample inlet conduit 26. Thus, in the operation of the zero gas circuit, the first on-off valve 36 is opened while the second on-off valve 37 is simultaneously closed by their respective solenoid actuators so that a zero gas is admitted to the second pump 35p through valve 36 while all gas from the monitored sample location where the integrator 26a is situated is prevented from entering the system through pump 25p.

In the preferred embodiment of the invention the gas monitor is adapted for use with a plurality of different sampling integrators that are located respectively in a number of different monitoring environments. Due to the novel arrangement of the control circuits of the present invention, it is possible to connect a number of such additional monitors to the system upstream from the second pump 25p in the gas sampling circuit. However, in order to simplify the description of the invention, only one such additional gas sampling inlet conduit 38, having a third on-off valve 39 and an associated gas integrator 40, is illustrated as being connected in the system for introducing gas from one additional inlet conduit 38 to the input side of the pump 25p. Of course, in the operation of the zero gas circuit when the first on-off valve 36 is actuated to introduce zero gas to the pump 25p, both the second and third on-off valves 37 and 38 will simultaneously be closed to prevent any gas from entering pump 25p from the monitored, potentially toxic gas environments. It has been found that about four or five spaced environments can be reliably sampled in rapid sequence with the disclosed monitoring system without impairing the accuracy of the single sensor 1 used therein. Thus at least three more inlet conduits could be connected at the junction of conduits 26 and 38, upstream from second pump 25p, if desired.

As was the case with the operation of calibration circuit described above, with the preferred solenoid control arrangement of the zero gas circuit, it is possible in this embodiment of the invention to periodically and readily introduce zero gas into the isolated series circuit A, including sensor 1, in order to either purge the sensor system, or to alternatively intermix the zero gas with the standard gas leak gas (from leak 29) in order to calibrate the sensor 1. Thus, the desired objectives of the invention pointed out above are provided in the optimum manner indicated.

Finally, in the preferred circuit arrangement shown in the drawing, a suitable conventional flow meter 41 is connected in series between the second pump 25p and the three-way valve 27. To calibrate this flow meter, a by-pass valve 48 is connected in parallel with it as indicated. In operation, the by-pass valve 48 will be normally adjusted to accurately meter a desirable gas flow through the flow meter 41.

From the foregoing description of the invention it will be apparent that various alternative embodiments and modifications may be made in it without departing from the true spirit and scope of the invention. Accordingly, it is my intention to encompass within the following claims the true scope of the invention.

What I claim as new and desire to secure by Letters Patent of the United States is:

1. A pneumatic system for controlling admission of a gas sample to a gas sensor comprising:
    a. a series loop cicuit including a gas sensor, a flow meter, a pump, a first manifold valve operably connected in the series circuit downstream from said pump to regulate gas flow between it and the sensor, a second manifold valve operably connected downstream from the sensor between it and the pump to regulate gas flow to said flow meter,
    b. a vented gas sample input chamber including an overflow gas input orifice connected to receive gas from a point in said series loop circuit between said pump and a first flow restricting needle valve in said first manifold valve, an outlet orifice connected to deliver gas to the first manifold valve, and a sample gas inlet orifice disposed between said overflow input orifice and said outlet orifice and operable to deliver a gas sample into said input chamber, and
    c. a bleeder line operably connected between the first and second manifold valves to bypass some gas received from the gas sample input chamber around said sensor, whereby said pump is effective when operated in said series loop circuit to force gas through said manifold valves, flow meter and sensor and to cause gas to flow continuously through the bleeder line and said manifold valves both during intervals when a sample gas is being introduced to the series loop and during intervals when sample gas is not being fed into the loop.

2. An invention as defined in claim 1 wherein said pump is a fixed displacement pump driven by a synchronous motor.

3. An invention as defined in claim 2 wherein each of said manifold valves includes, respectively, first, second and third chambers, a first adjustable needle valve disposed to control gas flow between said first and second chambers, and a second adjustable needle valve disposed to control gas flow between said second and third chambers.

4. An invention as defined in claim 3 wherein each of said first valve chambers is provided with an inlet orifice and an outlet orifice in addition to the needle valve regulated orifice therein communicating with its associated second valve chamber, said unregulated inlet and outlet orifices in the first chambers being connected respectively to bypass gas around the needle valve regulated orifice between said first and second chambers.

5. An invention as defined in claim 4 wherein the second chamber of the first manifold valve is provided with an outlet orifice connected in said series loop circuit to the sensor, and wherein the second chamber of the second manifold valve is provided with an outlet orifice connected in said series loop circuit in communication with the pump.

6. An invention as defined in claim 5 wherein said flow meter is operably connected in said series loop circuit between the unregulated outlet orifice of the first chamber in the second manifold valve and an inlet orifice in said second chamber of said second manifold valve.

7. An invention as defined in claim 6 including a gas purifier operably connected in said series loop circuit between the second manifold valve and the pump, and further including a gas filter operably connected in said series loop circuit between the sensor and said second manifold valve.

8. An invention as defined in claim 7 wherein the first needle valve in the first manifold valve is adjusted to cause gas to be pumped into said vented gas sample input chamber and to cause a vacuum pressure to be developed in the second chamber of the first manifold valve responsive to operation of the said pump.

9. An invention as defined in claim 8 wherein said first needle valve in the second manifold valve is adjusted to cause about half of the gas flow in said series loop circuit to pass through said flow meter.

10. The invention defined in claim 1 in combination with a gas sampling circuit comprising a second pump connected in series between a gas sample inlet conduit and a first three-way valve, with one outlet of said first three-way valve being in communication with the sample gas inlet orifice in said vented gas sample input chamber, and the other outlet of said three-way valve being in communication with a vent to the ambient atmosphere.

11. The invention defined in claim 10 in combination with a calibrating circuit comprising a selectively operable standard gas leak mounted to discharge gas into a chamber that is connected in series between said other outlet of the first three-way valve and a second three-way valve having its inlet connected to the standard gas leak chamber, with one of its outlets connected to said vent to the ambient atmosphere and with its other outlet connected in communication with the sample gas inlet orifice of said vented gas sample input chamber.

12. An invention as defined in claim 11 wherein discharge of gas from said selectively operable standard gas leak is controlled by a solenoid.

13. The invention defined in claim 11 in combination with a zero gas circuit comprising ambient air inlet conduit connected in series with an air purifier and a first on-off valve, and with the outlet of said on-off valve being connected to the upstream side of said second pump.

14. An invention as defined in claim 13 in combination with a second on-off valve connected in series between said second pump and said gas sample inlet conduit, said second on-off valve being operable to close responsive to the first on-off valve being opened to admit a zero gas to the second pump.

15. A pneumatic system for controlling admission of a gas sample to a gas sensor comprising:
- a. a series loop circuit including a gas sensor, a first pump, a flow meter and adjustable valves and bypass means for regulating the flow of gas through said sensor and said flow meter,
- b. a gas sample input chamber having an overflow input orifice in communication with a relatively high pressure portion of the series loop circuit and having an outlet orifice connected to deliver gas to a relatively lower pressure portion of said series loop circuit, and
- c. a gas sampling circuit comprising a second pump connected in series between a gas sample inlet conduit and the sample gas inlet orifice in said input chamber.

16. An invention as defined in claim 15 wherein said gas sampling circuit includes a standard gas leak connected in series between one outlet of a first three-way valve and an inleet of a second three-way valve, the first three-way valve having its inlet in communication with the downstream side of said second pump and having its other outlet connected in communication with the other outlet of the second three-way valve and the sample gas inlet orifice of said gas sample input chamber, said first and second three-way valve being selectively operable to pass all of the output gas from the second pump in mixing relationship with gas from said standard gas leak and thence into said input chamber.

17. An invention as defined in claim 15 including a zero gas input circuit connected to supply gas to the second pump, and on-off valve means for closing said gas sample inlet conduit responsive to the zero gas input circuit supplying gas to said second pump.

18. An invention as defined in claim 15 including at least one additional gas sample inlet conduit having a third on-off valve connected therein for controlling flow of gas from the additional inlet conduit to the input side of said second pump.

* * * * *